US012797222B2

(12) United States Patent
Saier et al.

(10) Patent No.: US 12,797,222 B2
(45) Date of Patent: Nov. 17, 2026

(54) DYNAMICALLY DEPENDENT MOVEMENT BLOCKING SYSTEM

(71) Applicant: O'NEAL EUROPE GMBH & CO. KG, Vaihingen an der Enz (DE)

(72) Inventors: Thomas Saier, Klagenfurt (AT); Dietmar Rafolt, Granz (AT); Peter Schreckensberger, Schwanenstadt (AT); David Russ, St. Nololai im Sausal (AT); Eduard Falk, Granz (AT)

(73) Assignee: O'NEAL EUROPE GMBH & CO. KG, Vaihingen an der Enz (DE)

( * ) Notice: Subject to any disclaimer, the term of this patent is extended or adjusted under 35 U.S.C. 154(b) by 251 days.

(21) Appl. No.: 18/705,121

(22) PCT Filed: Nov. 2, 2022

(86) PCT No.: PCT/EP2022/080498

§ 371 (c)(1),
(2) Date: Apr. 26, 2024

(87) PCT Pub. No.: WO2023/078893

PCT Pub. Date: May 11, 2023

(65) Prior Publication Data

US 2025/0228690 A1 Jul. 17, 2025

(30) Foreign Application Priority Data

Nov. 2, 2021 (AT) .................................. 60272/2021

(51) Int. Cl.
*A61F 5/01* (2006.01)

(52) U.S. Cl.
CPC ...... *A61F 5/013* (2013.01); *A61F 2005/0155* (2013.01); *A61F 2005/0167* (2013.01)

(58) Field of Classification Search
CPC ........ A61F 5/01; A61F 5/0102; A61F 5/0123; A61F 5/0127; A61F 5/013; A61F 2005/0169
See application file for complete search history.

(56) References Cited

U.S. PATENT DOCUMENTS

| | | | |
|---|---|---|---|
| 4,741,115 | A | 5/1988 | Pozzobon |
| 5,165,510 | A | 11/1992 | Lunati |
| 5,712,011 | A | 1/1998 | McMahon et al. |
| 5,762,599 | A | 6/1998 | Sohn |
| 6,033,334 | A | 3/2000 | Showalter |
| 6,202,953 | B1 | 3/2001 | Hammerslag |
| 7,591,050 | B2 | 9/2009 | Hammerslang |

(Continued)

FOREIGN PATENT DOCUMENTS

| | | | |
|---|---|---|---|
| DE | 102016114110 | A1 | 2/2018 |
| DE | 102017109877 | A1 | 11/2018 |

(Continued)

*Primary Examiner* — Keri J Nelson
(74) *Attorney, Agent, or Firm* — Shumaker, Loop & Kendrick, LLP

(57) ABSTRACT

A dynamically dependent blocking system for orthoses or protectors for limiting relative movements of at least two body segments consisting of at least one blocking unit having a blocking element, an extending element and the body attachment structures, and worn on the body. The central element of the blocking unit is the blocking element.

18 Claims, 10 Drawing Sheets

(56) References Cited

U.S. PATENT DOCUMENTS

| | | | |
|---|---|---|---|
| 7,811,333 | B2 | 10/2010 | Jonsson et al. |
| D663,850 | S | 7/2012 | Joseph |
| D666,301 | S | 8/2012 | Joseph |
| D666,302 | S | 8/2012 | Joseph |
| 8,277,401 | B2 | 10/2012 | Hammerslang et al. |
| 8,597,369 | B2 | 12/2013 | Hansen et al. |
| 8,696,764 | B2 | 4/2014 | Hansen et al. |
| 8,968,227 | B2 | 3/2015 | Rokosz et al. |
| D758,061 | S | 6/2016 | Whewell |
| 10,098,775 | B2 | 10/2018 | Bichler et al. |
| 2010/0032239 | A1 | 2/2010 | Rinklake et al. |
| 2011/0031800 | A1 | 2/2011 | Motozawa |
| 2012/0209405 | A1 | 8/2012 | Herr et al. |
| 2017/0304057 | A1 | 10/2017 | Bichler et al. |
| 2018/0037191 | A1* | 2/2018 | Franz .................. B60R 22/4633 |
| 2021/0030575 | A1 | 2/2021 | Bichler et al. |
| 2021/0137722 | A1* | 5/2021 | Arai ........................ A61F 5/028 |

FOREIGN PATENT DOCUMENTS

| | | | |
|---|---|---|---|
| DE | 102017117786 | B4 | 5/2019 |
| EP | 0368798 | B1 | 9/1993 |
| EP | 0682483 | B1 | 9/1993 |
| EP | 2584720 | B1 | 3/2017 |
| EP | 3145455 | B1 | 5/2018 |
| EP | 3294236 | B1 | 7/2019 |

* cited by examiner

Fig. 16
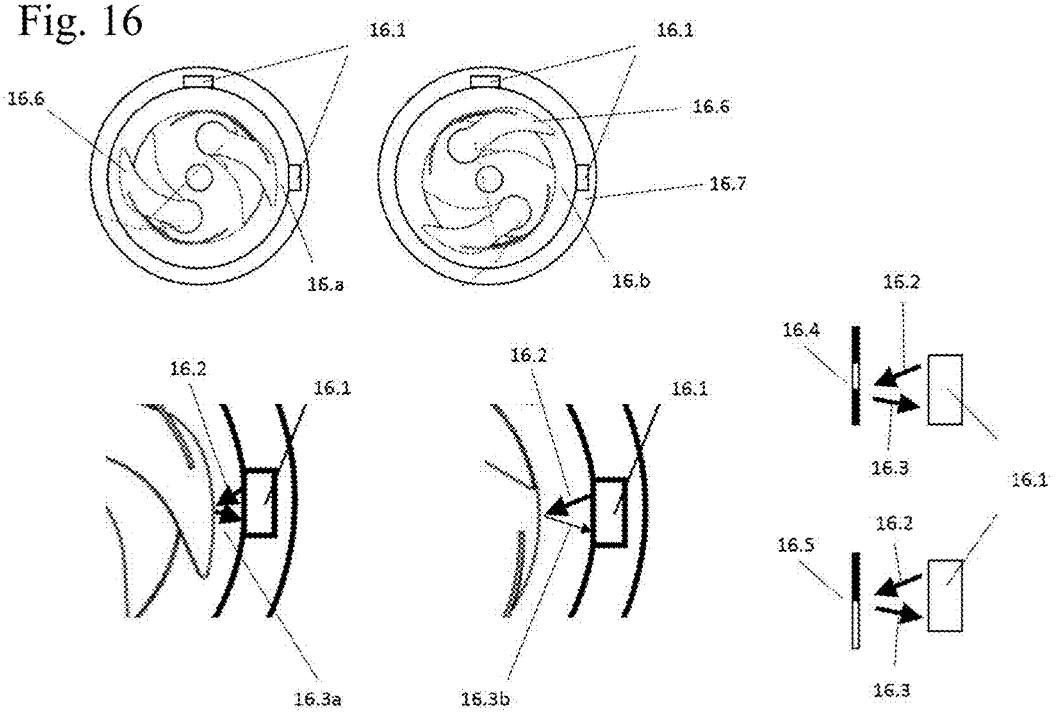
Fig. 17
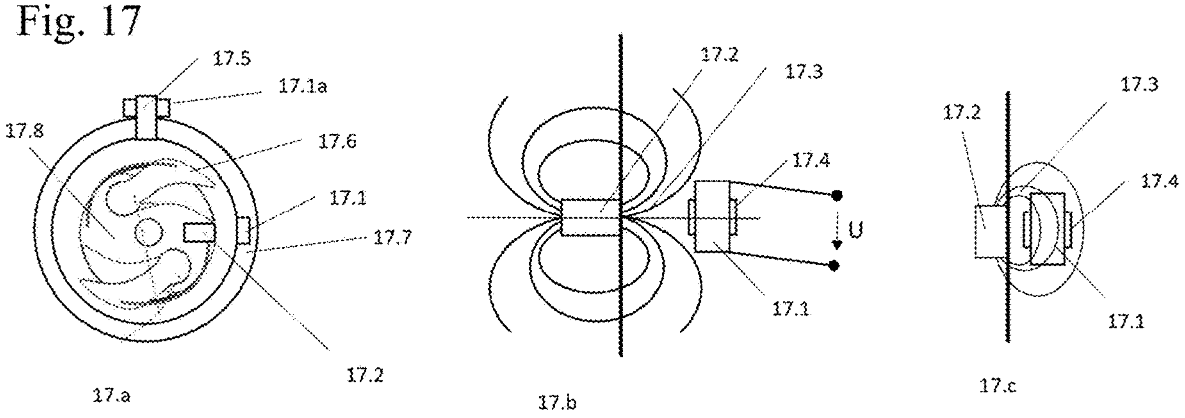
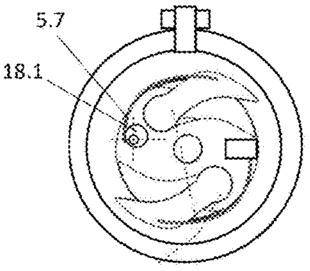
Fig. 18

DYNAMICALLY DEPENDENT MOVEMENT BLOCKING SYSTEM

CROSS-REFERENCE TO RELATED APPLICATIONS

This is a U.S. national phase patent application of PCT/EP2022/080498 filed Nov. 2, 2022 which claims the benefit of and priority to Austrian Patent Application No. A 60272/2021, filed Nov. 2, 2021, the entire contents of each of which are incorporated herein by reference.

FIELD

The present invention relates to a dynamically dependent blocking system, and more particularly to a dynamically dependent blocking system for orthoses or protectors for limiting relative movements of at least two body segments.

BACKGROUND OF THE INVENTION

Based on the current PPE (personal protective equipment) regulation of CEN Standard 1621, existing body protectors are only designed for direct impacts to the body. The medical perspective confirms that the overwhelming majority of bodily injuries are attributed to the natural physiological ranges of motion of the human body being exceeded.

The present patent application describes structures able to prevent physiological exceedances in the respective regions of the body.

These structures consist of:

attachment structures to joint segments, as well as connecting structures between the respective attachment structures.

Defining the efficiency of connecting structures on the human body requires consideration of the fact that in addition to hard bony structures, elastic tissue such as cartilage, muscle, connective tissue, fat, etc. must also be factored into the transmission of forces. Elasticities and compressibilities come into play depending on how the lines of force run when using connecting structures affixed to the respective attachment structures. Additional dynamic processes can also intensify this, potentially occurring when, for example, lines of force on the exterior of the human body are conducted away from the neutral bending line (14.2) (FIG. 14). This problem increases in the case of cascaded joint segments such as the spine.

This is evident in the protections used in athletics and workplaces, and particularly in rehabilitation, since in order to protect against injuries, movement needs to be restricted by blocking the body segments prior to the segments experiencing maximum deflection.

The invention is therefore based on the object of describing a blocking element as shown and described herein which is integrated into a connecting structure, allows the natural movement of body segments depending on speed and deflection angle, and initiates blocking upon a speed threshold.

Prior Art

The following prior art was compiled in the course of researching: EP2854720B1; EP3145455B1; US10 098775B2; EP3294236B1; US 20170304057A1; DE 102017117786B4; DE102018116569B3; DE 102016114110A1; DE 102017109877A1; EP0368798B1; EP0682483B1; U.S. Pat. Nos. 4,741,115; 6,202,953B1; 7,591,050B2; 8,277,401B2; USD663850S; USD666301S; USD666302S; USD 758061S; U.S. Pat. Nos. 8,597,369B2; 5,762,599A; 6,033,334A; 8,968,227B2; 20,120,209405A1; 7,811,333B2; 8,696,764B2; US20100032239A1; U.S. Pat. No. 5,165,510A; US20110031800A1

SUMMARY

In contrast to patent: EP2854720B1; EP3145455B1; US10 098775B2; EP3294236B1; US 20170304057A1; DE 102017117786B4; DE102018116569B3; DE 102016114110A1; DE 102017109877A1, the present invention is differentiated by its use of predominantly mechanical and/or electronic locking mechanisms. The properties of viscous liquids are temperature-dependent. Thus, with mechanisms dependent on the properties of viscous liquids, it is difficult to achieve the same triggering properties within a temperature range of from e.g. −40° Celsius to +50° Celsius. The advantage of mechanical locking (present invention) is that temperature fluctuations only have very minor influence on the component's blocking properties.

In contrast to patent: EP0368798B1; EP0682483B1; U.S. Pat. Nos. 4,741,115; 6,202,953B1; 7,591,050B2; 8,277,401B2; USD663850S; USD666301S; USD666302S; USD 758061S, the present invention is differentiated by the system not being intended for lacing together opposite sides of clothing. The present invention works on the same principle as a seatbelt. The inventive device is movable below a defined speed threshold and only locks up above this threshold with the aid of a blocking mechanism.

The basic principle of the present invention consists of a rotor (5.4), onto which an extending element (1.4) in the form of a cable, belt, etc. is wound, being blocked by a blocking mechanism (1.1.3) as of a specific speed and further extending of the extending element (1.4) being prevented, whereby the two body segments connected together by the blocking system (1.1) cannot move further apart from each other. This for example being an extending of the elbow when the upper arm and forearm are connected more or less parallel to the biceps or a rotating of the upper body when the shoulder and hip regions are connected together diagonally by the blocking mechanism.

Blocking occurs by means of a contact element (5.6) pushed outward due to centrifugal force. For the centrifugal force to move the contact element (5.6), its pivot point must lie outside the center of mass. As of a specific deflection, the contact element (5.6) positively catches into a positive locking structure (5.3) on the stator (housing) and the rotation is stopped. The centrifugal movement results from the centrifugal force and the force of a return leaf spring (5.7) which pulls the contact element (5.6) back inward again at low speed. The stiffness of this spring determines the triggering speed and can vary.

The blocking system (1.1) thus comprises two planes. The blocking mechanism (1.1.3) is located in the first plane close to the body and the winding mechanism (1.1.2) is in the second plane, wherein the order is arbitrary.

With the same arrangement, albeit without an interlocking profile in the positive locking structure (5.3), blocking by means of a slip clutch (similar to a drum brake) can be realized. The higher the speed, the greater the braking effect, which is able go down to a relative movement of 0.

This self-triggering system draws the energy for activating the blocking exclusively from the extending mechanism itself, thus from body segment movements. The mass of the contact element (5.6) as well as the spring force of the return spring (5.7) are constant and hence also the extending speed of the extending element (1.4) which initiates blocking. The behavior can be defined by varying these two components. An eccentric adjusting screw (18.1) which varies the pretension of the leaf spring can be used to that end (FIG. 18).

Controlled Blocking System with Auxiliary Energy:

A further new device presented here draws the energy for blocking from an electromagnetic system. That means that no centrifugal force is needed, instead the rotating part and the stationary part each have a mutually positive structure which are brought together via the auxiliary energy. In the de-energized state, the parts are separated from each other and have no frictional connection. The auxiliary energy moves the parts towards each other and into a positive locking engagement, which effects the blocking (FIG. 12).

For safety reasons, the function can be reversed so that blocking is activated in the absence of auxiliary energy and motion enabled by auxiliary energy.

This blocking system with auxiliary energy offers the possibility of triggering blocking at any time regardless of speed. The triggering can be induced by various types of sensors such as acceleration sensors, gyrometers or force sensors. If acceleration sensors are affixed to the attachment structures, for example, the extending speed can be determined from subtraction and integration and the joint rotation speed determined via the geometry. The same information can be obtained from the difference between two gyrometers fit on the upper and lower arm or on the shoulder and hip, for example. The latter captures upper body rotation and thus rotation of the spine. Calculating the difference is important because the body usually moves through space as a whole. The information about the change in length between the attachment structures can also come from the blocking element (1.1) itself when using an integrated speed sensor or rotational position sensor as depicted in FIG. 17.

Furthermore, the data from these sensors can be linked to other parameters and information in order to trigger the blockage via an algorithm. Moreover, the current sensor data can predictively calculate an accident situation. Whether the normal physiological deflections of body segments will be exceeded is apparent from the different body segment trajectories.

Knowledge about the driving behavior of those wearing protective wear is also helpful thereto, this likewise being able to be captured using the described sensors. This information can be obtained from the current driving style or also from saved previous drives. This also makes it possible to identify a poor or respectively unsafe driver, whereby the blockage response threshold can be reduced and vice versa. The triggering algorithms can also incorporate further information coming from a complex information network, e.g. with other drivers and instructors or even from GPS.

When multiple blocking units are used on multiple body segments, an optimal processor-controlled blocking sequence can be defined so that the different inertia components of the human body are factored into the dynamic accident situation and the accident ends up being as protective of the spine as possible, for example (FIG. 8).

Combination self-triggering and active blocking systems can be achieved by utilizing the rotor arrangement with the centrifugal force principle of the self-triggering system but the positive counterpart in the stator being movable via auxiliary energy so that the positive locking will or will not occur as described (FIG. 19). The positive locking structure (5.3) is axially displaceable to that end. When fully extended, the contact elements (5.6) can be centrifuged outward by the rotation yet do not achieve a positive locking and thus not trigger a blockage. The previously described blockage does not occur until the locking structure (5.3) is retracted into the structure. The locking structure can also have a conical inner structure (19.1), whereby depending on how far the locking structure is retracted, the air gap and thus the deflection path of the blocking element (5.6), and consequently the blockage triggering, vary. Marginal auxiliary energy can therefore be used to adjust the triggering speed. For example, the axial displacement can ensue by the positive locking structure (5.3) being seated on a fine thread on the housing and rotated by a stepper motor via a gear or belt drive and thus being displaceable in the axial direction. This adjustment can also be made manually. The triggering would thus be adjustable yet fixed for a person or application.

DESCRIPTION OF THE FIGURES

FIG. 16 is a schematic diagram showing use of reflected light sensors which are implemented in the housing and detect when the contact elements pass the sensor during rotation.

FIG. 17 is a schematic diagram showing an embodiment of how electrical energy can be obtained from the movement of body segments relative to each other using a blocking system.

FIG. 18 is a schematic diagram showing an embodiment using an eccentric to variably pretension a leaf spring.

DESCRIPTION OF AN EMBODIMENT

Figure 1:
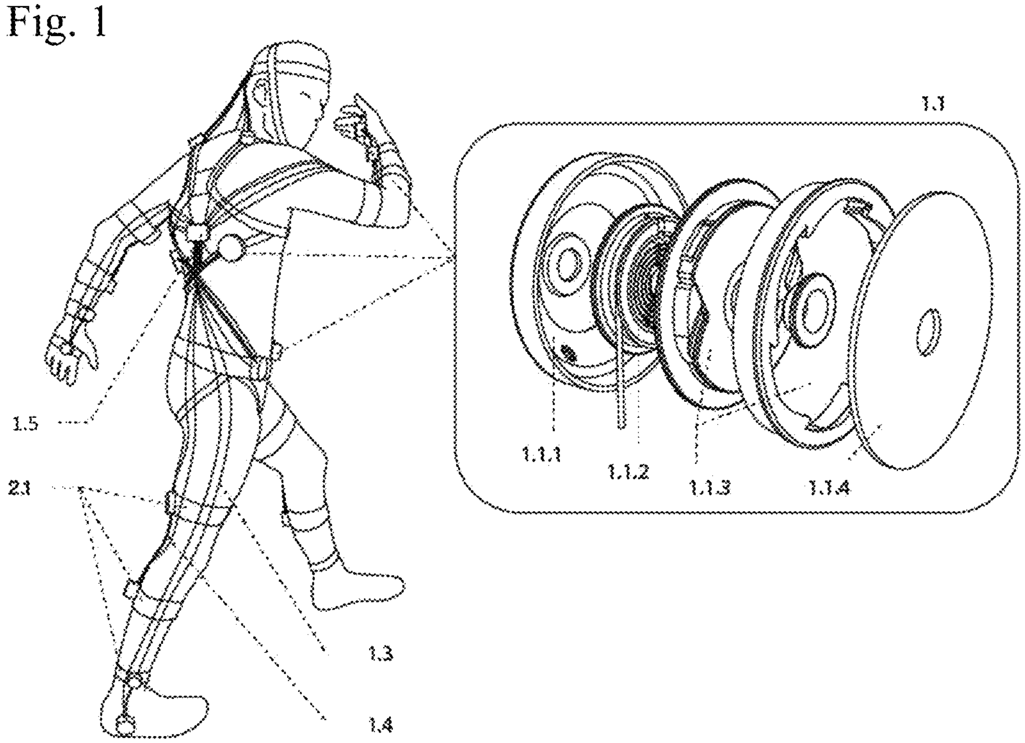
FIG. 1 is a schematic diagram showing a person in motion outfitted with a blocking system according to an embodiment of the invention.

FIG. 1 shows a person in motion outfitted with the blocking system consisting of several blocking units (1.0). The blocking units (1.0) are comprised of blocking elements (1.1) and tension elements (1.4) which are affixed to the body attachment structures (2.1). The blocking elements (1.1) consist of a housing (1.1.1, 1.1.4), a winding mechanism (1.1.2) and a blocking mechanism (1.1.3).

The individual blocking elements (1.1) can be connected to a central control and triggering device (1.5) via control lines (1.3).

Figure 2:
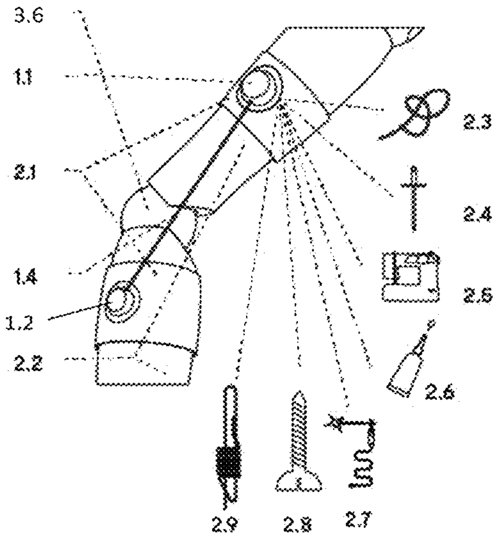
FIG. 2 is a schematic diagram showing two body segments.

FIG. 2 shows two body segments (2.2), connected by a hinge joint (3.6), to which a body attachment structure (2.1) is affixed and on which a blocking element (1.1) is affixed and connected by means of a tension element (1.4). The blocking element can be connected to the body attachment structure (2.1) by tying (2.3), riveting (2.4), sewing (2.5), gluing (2.6), welding (2.7), screwing (2.8) and wiring (2.9). The blocking element (1.1) can also be used on only one side of the joint, whereby the load cable is connected to the corresponding attachment structure (2.1) via the tension connection (1.2).

Figure 3:
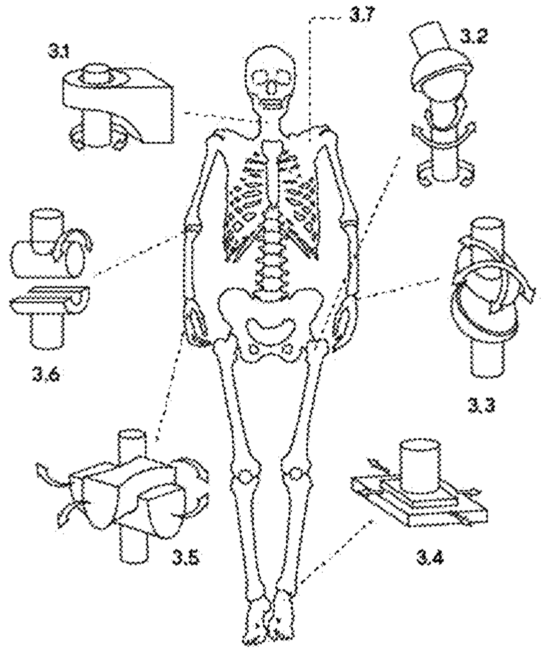
FIG. 3 is a schematic diagram showing a human skeleton with different body segments.

FIG. 3 depicts a human skeleton (3.7) with different body segments (2.2) connected by swivel joints (3.1), ball joints (3.2), condylar joints (3.3), planar joint connections (3.4), saddle joints (3.5), hinge joints (3.6).

Figure 4:
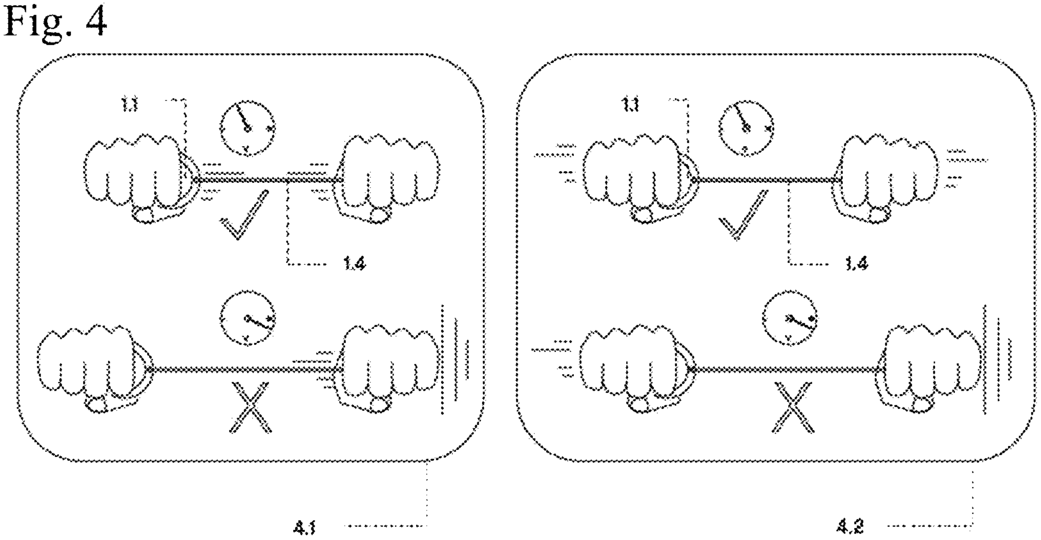
FIG. 4 is a schematic diagram showing two hands respectively pulling apart or pressing together a blocking element and a tension element.

FIG. 4 shows two hands respectively pulling apart (4.1) or pressing together (4.2) a blocking element (1.1) and the other end of a tension element (1.4). It can be seen here that the blocking element is freely movable below a defined speed threshold but blocked above a defined speed threshold.

Figure 5:
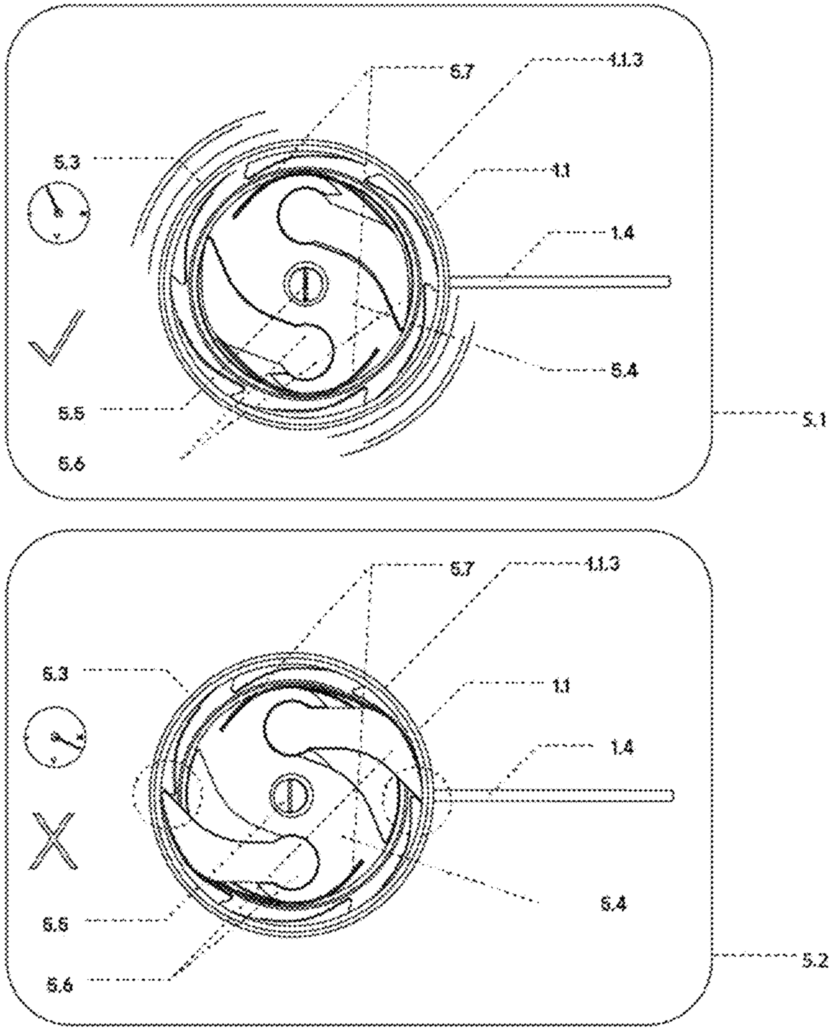
FIG. 5 is a schematic diagram showing a blocking mechanism of a blocking element.

FIG. 5 shows a blocking mechanism (1.1.3) of a blocking element (1.1) from above, which is actuated by the tension element (1.4). Detail (5.1) shows the state below a defined speed threshold where the return spring (5.7) is stronger than the centrifugal force on the contact elements (5.6) and thus the blocking mechanism (1.1.3) is freely movable. The mounted receiving disk (5.4) with the spring-returned contact elements (5.6) situated therein can freely move around the spindle (5.5).

Detail (5.2) shows the state after a defined speed threshold has been exceeded, with the blocking mechanism (1.1.3) being positively blocked by the surrounding positive locking structure (5.3). The extending element (1.4) is deflected in the tangential direction of the winding mechanism (1.1.2) either during or after entering the blocking element (1.1).

The direction of the extending element (1.4) runs to the center and is deflected at the housing tangentially to the winding mechanism (1.1.2). No torque is thereby generated between the housing and the attachment structure (2.1) during blocking. When allowed, the extending element (1.4) can also exit the housing eccentrically, tangential to the winding mechanism (1.1.2).

Figure 6:
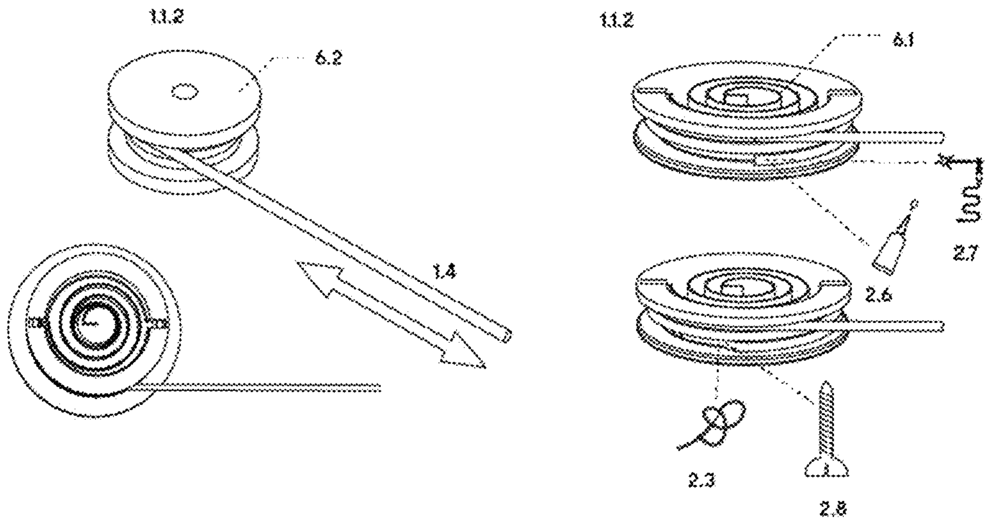
FIG. 6 is a schematic diagram showing a resetting winding mechanism powered by an energy store.

FIG. 6 shows a resetting winding mechanism powered by an energy store such as a spiral spring (6.1). The tension element (1.4) is thereby variably extendable and can be connected to the coil thermally (e.g. welding) (2.7), mechanically (e.g. tying) (2.3), by screwing (2.8) or chemically (e.g. gluing).

Figure 7:
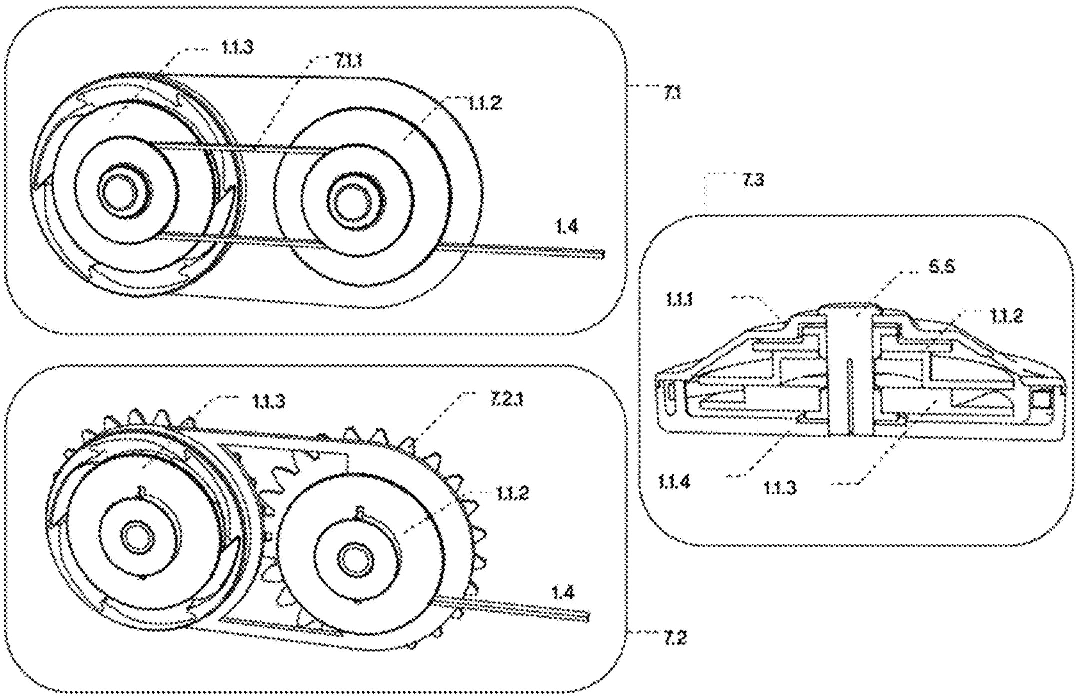
FIG. 7 is a schematic diagram showing three variants of the blocking element in which the winding mechanism as well as the blocking mechanism are arranged to transmit force radially and axially to each other.

FIG. 7 shows three variants of the blocking element (1.1) in which the winding mechanism (1.1.2) as well as the blocking mechanism (1.1.3) are arranged to transmit force radially and axially to each other. Detail 7.1 shows a radial arrangement of the winding mechanism (1.1.2) and the blocking mechanism (1.1.3) which are frictionally connected by a belt (7.1.1).

Detail 7.2 shows a radial arrangement of the winding and blocking mechanism (1.1.3), (1.1.2) which are frictionally connected to each other by gearing (7.2.1).

(7.3) shows a sectional view through the blocking unit (1.1) in which the winding mechanism (1.1.2) and the blocking mechanism (1.1.3) are frictionally connected via a spindle (5.5) and encased in a housing (1.1.1/1.1.4).

Detail 7.1 and detail 7.2 have the advantage of the arrangement becoming flatter.

Figure 8:
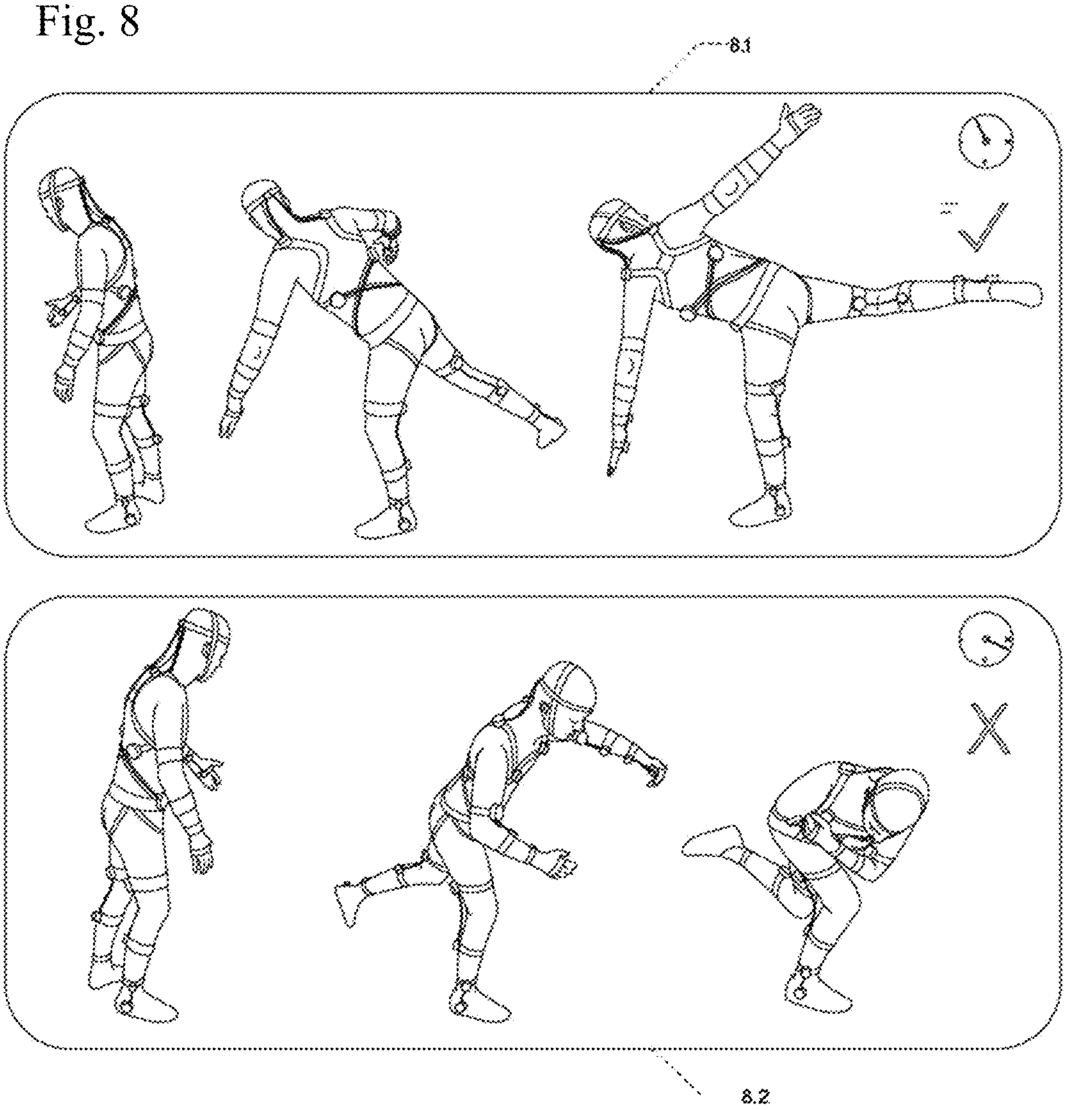
FIG. 8 is a schematic diagram showing a motion sequence of accidents in two three-part sequences.

FIG. 8 shows the motion sequence of accidents in two three-part sequences.

Detail 8.1 shows the unrestricted freedom of movement at a defined speed. Detail 8.2 shows an accident in which the blocking units (1.1) block and thus protect the joints from excessive physiological stress.

Figure 9:
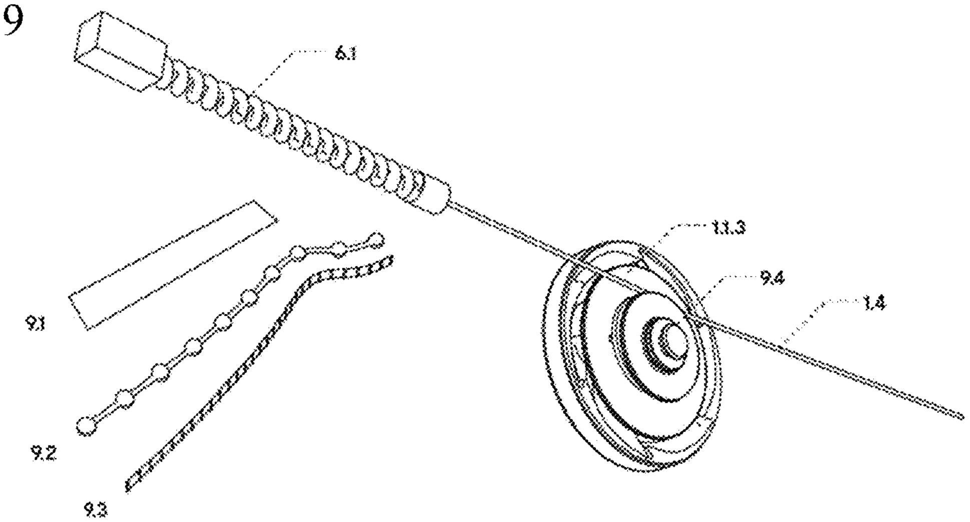
FIG. 9 is a schematic diagram showing an embodiment in which the energy store for tightening the extending element and for rewinding onto the coil body is affixed externally.

FIG. 9 shows one embodiment variant in which the energy store (6.1) for tightening the extending element (4.1) and for rewinding onto the coil body (6.2) is affixed externally. Transmission of power ensues via a deflection mechanism (9.4) affixed to the blocking element (1.1.3). The tension element (1.4) can be designed as a cable (1.4), chain (9.2), belt (9.3) or strap (9.1).

Figure 10:
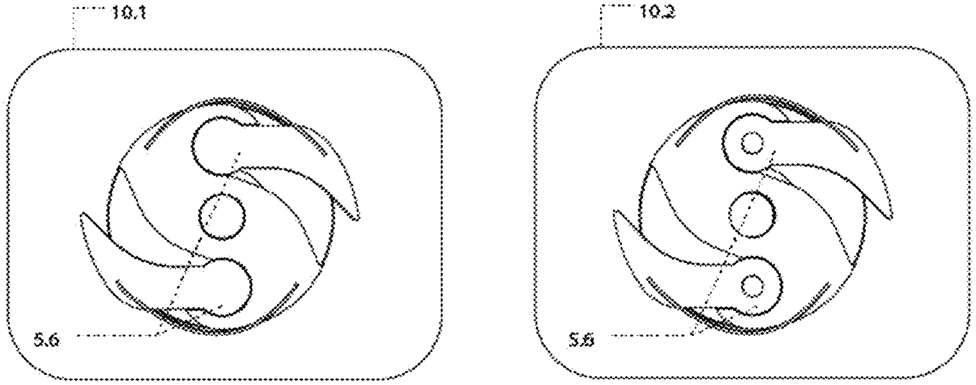
FIG. 10 is a schematic diagram showing embodiments in which contact elements can be embedded via a concentric positive fit or via a bearing bolt.

FIG. 10 shows two embodiment variants in which the contact elements (5.6) can be embedded via a concentric positive fit (10.1) or via a bearing bolt (10.2). Both illustrations constitute a cylindrical bearing with radial and axial fixation, with rotational freedom restricted by limit stops. Also illustrated are the curved leaf springs (5.7) which act against the centrifugal force and centripetally return the contact elements (5.6) below a specific rotational speed.

Figure 11:
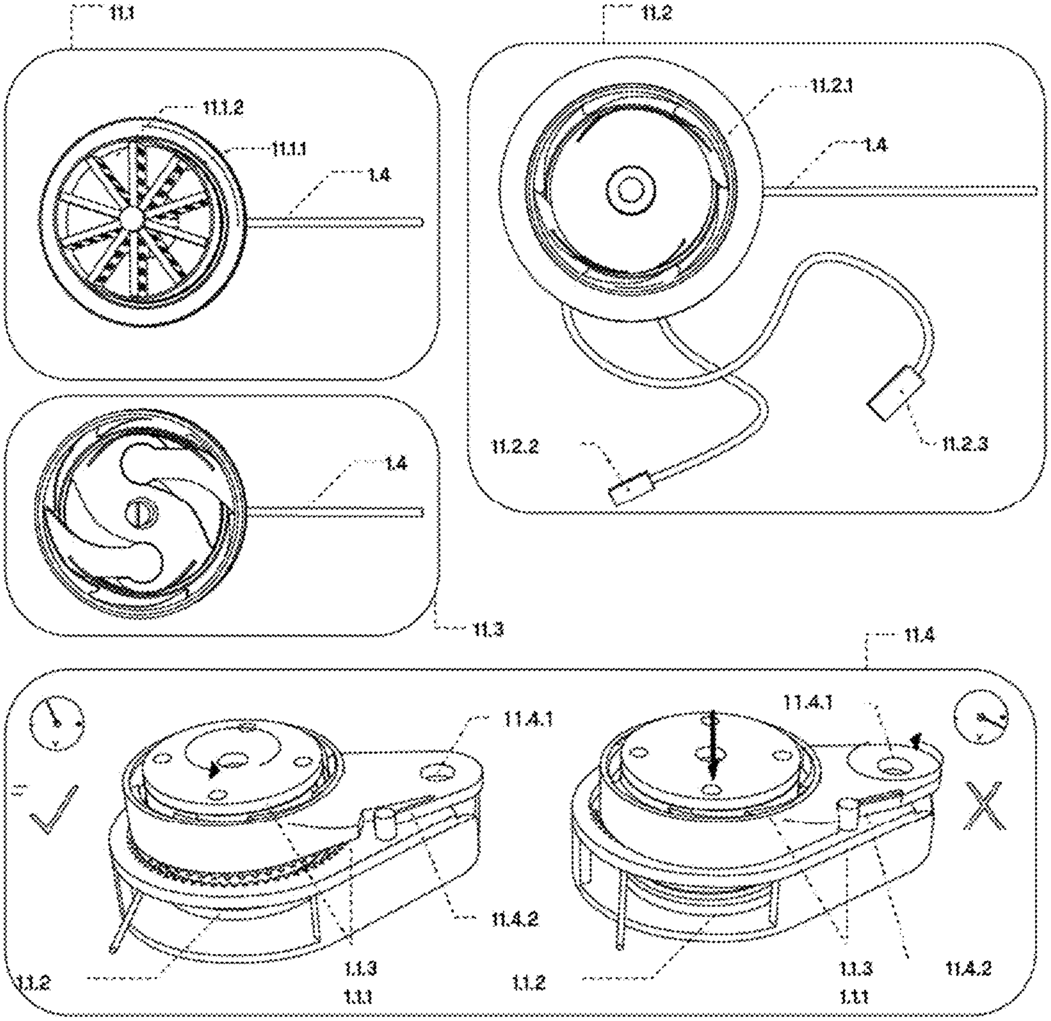
FIG. 11 is a schematic diagram showing embodiments of the blocking mechanism.

FIG. 11 shows three embodiment variants of the blocking mechanism (1.1.3). Detail (11.1) shows the blocking rotor (11.1.1) in a blade structure arrangement embedded in a preferably viscous liquid (11.1.2). This provides less resistance at low speed than at high speed. Moreover, at abruptly increasing speed, the liquid (11.1.2) cannot be deflected quickly enough and there is therefore more forceful blocking of the rotor of the blocking mechanism (1.1.3). The effect is heightened when the rotor blades are of, for example, strut-like structure (11.1.1) or have radial slits into which the rigid rake-shaped fins fixed to the stator engage.

Detail (11.2) shows an electromagnetic coupling with a respective speed sensor (11.2.2, 11.2.3) as well as an electromagnetic coil (11.2.1) which magnetically locks the blocking mechanism (1.1.3) at a defined speed.

Detail 11.3 shows a blocking mechanism (1.1.3) which allows the locking of the contact elements (5.6) by centrifugal force.

Detail (11.4) shows an exemplary embodiment of the blocking element (1.1) in which the blocking mechanism (1.1.3) is mounted axially with the winding mechanism (1.1.2) and mounted as a unit over a defined pivot point (11.4.1). This unit is held in a defined position below a load threshold via a spring return (11.4.2). Should the energy exceed the load threshold, the blocking unit with the mounting mechanism is positively pressed against the housing (1.1.1) via the defined pivot point and thus locked.

Figure 12:
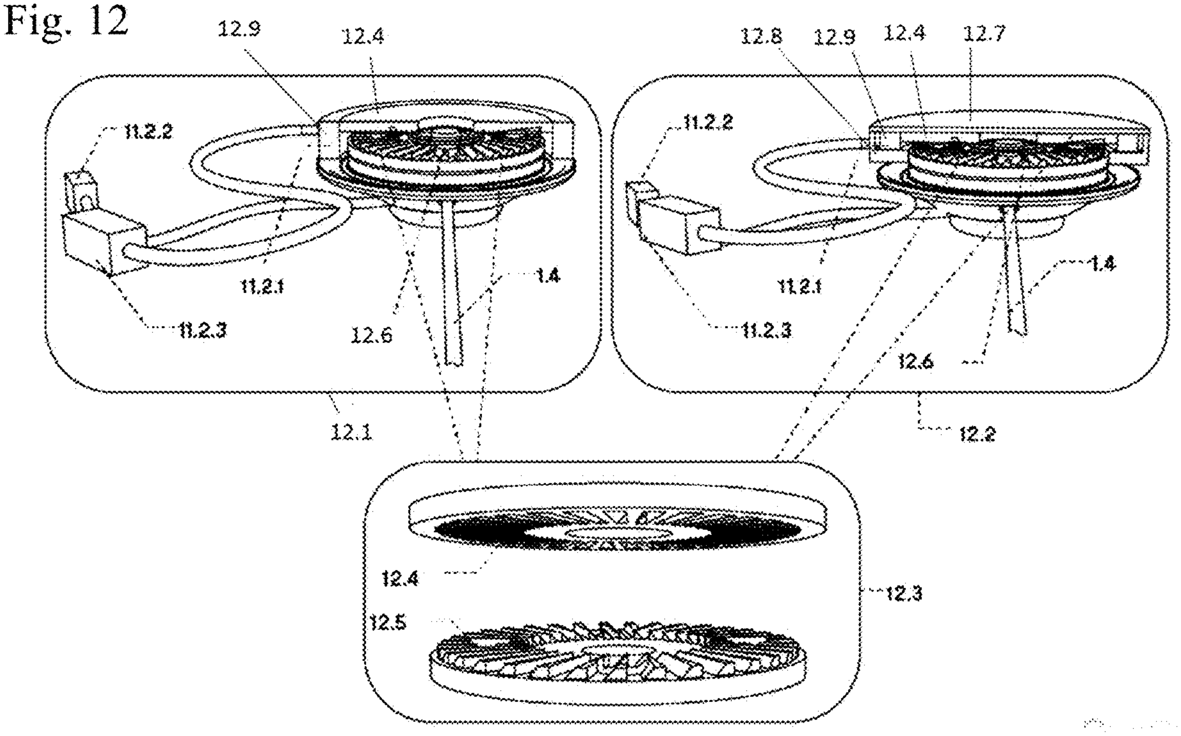
FIG. 12 is a schematic diagram showing embodiments of an electromagnetically controlled blocking unit.

FIG. 12 shows two exemplary designs of an electromagnetically controlled blocking unit. One variant with two axially arranged locking plates (12.4), (12.5) can be seen in detail 12.1, or in the detail 12.3 enlargement respectively, wherein (12.5) has axial displaceability yet torque can be transmitted to the spindle, for example via tongue and groove. (12.4) is rigidly connected to the stator. Without electromagnetic activation, the two plates are kept apart by a spring (12.6).

12.3. shows a detail view of (12.1) and (12.2) from a different angle with the two locking plates (12.4), (12.5) having complementary profiles for form-fit locking.

Blockage is realized in that the lower plate (12.5) engages positively in the upper plate (12.4), thereby achieving the generating of a magnetic field by an energized electric coil (12.2.1) enclosed by the housing part (12.2.7), the fixed plate (12.4), the rotating plate (12.5) and the annular yoke (12.8) and the exertion of attractive forces on the plates in the air gap between the plates (12.4) and (12.5). A frictional coupling can also be realized without a form-fit profile.

Detail 12.2 shows a further exemplary embodiment in which the housing (1.1.4, 1.1.1) encloses the electromagnetic coil (11.2.1).

Figure 13:
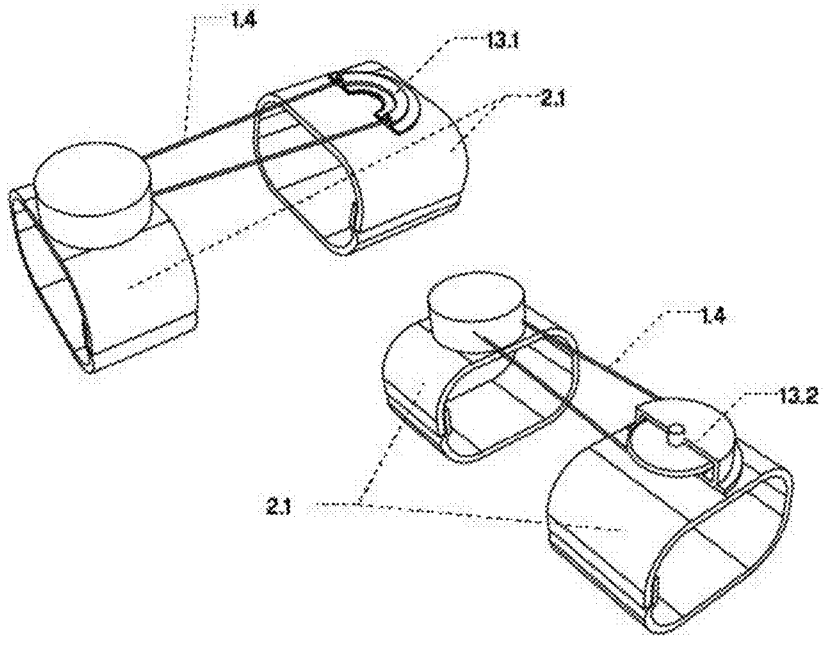
FIG. 13 is a schematic diagram showing two body attachment structures in which the blocking unit with tension element is coupled to itself by a deflection mechanism.

FIG. 13 shows two body attachment structures (2.1) in which the blocking unit (1.1) with tension element (1.4) is coupled to itself by a deflection mechanism (13.1, 13.2). This means that one side of the tension element (1.4) leads to the drum of the blocking system as previously described, whereby the other end of (1.4) leads to a fixed point on, for example, the housing of the blocking unit or the body attachment (2.1) itself via the deflection (13.1/13.2). The maximum load is thus doubled through the pulley principle. This is achieved using sliding surfaces (13.1) or supported cylindrical bodies (13.2).

At the same time the blocking force is doubled, the length of the cable drawn out of the coil is doubled, which leads to a doubling of the rotational speed in the same unit of time and consequently increases the centrifugal forces or viscous effects and thus the blocking or respectively braking function.

Figure 14:
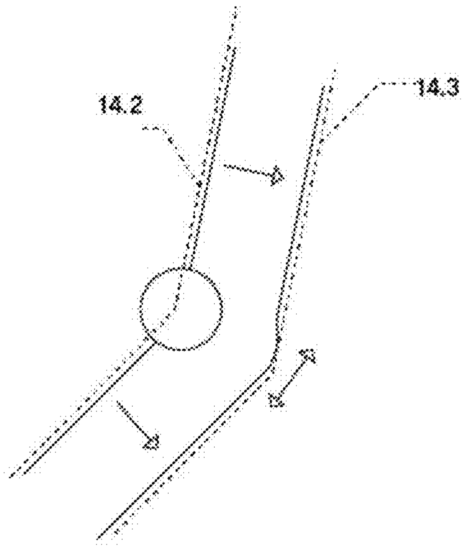
FIG. 14 is a schematic diagram showing an abstracted hinge joint of the human body.

FIG. 14 depicts an abstracted hinge joint of the human body, in which can be seen that a bend in the neutral fiber line (14.2) does not cause an offset in length. If the offset surfaces (14.3) are then offset parallel to the neutral fiber line (14.2), the change in length becomes significant with the distance from the pivot point.

Figure 15:
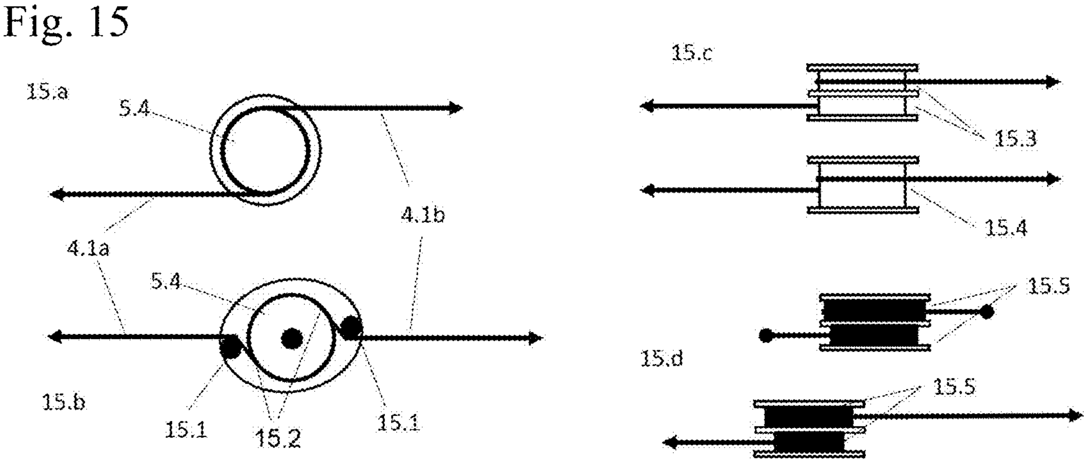
FIG. 15 is a schematic diagram showing an embodiment of a blocking system having two tension elements which lead from two opposite outlets in opposite directions along a line of force to the two body attachment structures.

FIG. 15 shows a further variant of a blocking system (1.1) having two tension elements (1.4*a*, 1.4.*b*) which lead from two opposite outlets in opposite directions along the line of force to the two body attachment structures (2.1). The two tension elements (1.4*a*, 1.4.*b*) are wound on the coil body (5.4) in the same directionality and can rest on top of (15.4) or adjacent each other in two separate winding chambers (15.3). The advantage here being that the blocking system (1.1) itself does not need to have any connectivity (sewing, gluing, riveting, etc.) to a body attachment structure (2.1) and that the housing can be of smaller design. There is also often little space in the body attachment structure such that a blocking system (1.1) would be disruptive there. When making use of two winding chambers (15.3) on the coil body, they can have different diameters (15.5), wherein the position of the blocking system (1.1) is not symmetrically located between the suspension points but rather shifts more towards one attachment point, whereby different types of joints and outfit designs can be considered.

(15.*a*) shows the basic principle of double winding in a vertical section, whereby (15.*b*.) shows the principle of a practical implementation containing two bolts (15.1) (15.1) in the housing which on the one hand deflect the tension elements (4.1*a*, 4.1*b*) into the tangent (15.1) of the winding mechanism (1.1.2) and at the same time constitute at least one bolt of the anchoring for the spiral spring. 15.*c* and 15.*d* show coil variants.

FIG. 16 shows the use of reflected light sensors (16.1) which are implemented in the housing (16.7) and detect when the contact elements (5.6), (16.6) pass the sensor during rotation. In position (16.*a*), a contact element (5.6) (16.6) is in front of the sensor, whereby the emitted light (16.2) is strongly reflected (16.3*a*). In position (16.*b*), the distance is greater and the emitted light (16.2) is less strongly reflected (16.3*b*). One or also multiple sensors can be used. Two sensors are depicted here. This makes it possible to also detect the rotational direction if the two sensors are at <90° positioning, e.g. 45°, or both catches have different light/dark surface coding (16.4) and (16.5). Preferably, a threshold is defined for "catch/no catch" and the signal is further processed digitally (time measurement).

The direction of rotation can also be measured with only one sensor if the reflected signal is recorded in analog. Due to the profile of the contact elements (5.6) (16.6), the measured curve of the reflected light indeed appears dependent on the rotational direction.

Instead of a reflected light sensor (16.1), a magnetic sensor in the form of a detector coil or a Hall sensor, or an ultrasonic sensor or a microphone capsule can also be used.

FIG. 17 shows one option of how electrical energy can be obtained from the movement of body segments relative to each other using a blocking system. To that end, a permanent magnet (17.2) is positioned in the rotating part (17.8) on the circumference or on one of the end faces near the circumference which induces a voltage in a fixed coil (17.1) via its magnetic field (17.3). The orientation of the magnet can be in the radial direction as depicted in detail 17.*b* or in the tangential direction (17.*c*). A coil core (17.4), e.g. of iron or ferrite, can be used to intensify the magnetic flux. If the coil is not integrated directly into the housing, the coil (17.1*a*) can also be positioned externally of the housing and the magnetic flux directed outward with a longer iron core (17.5). The braking effect during the rewinding of the extending element can be prevented if the load is disconnected in this phase using electronics.

FIG. 18 shows the option of using an eccentric (18.1) to variably pretension the leaf spring (5.7) and thus regulate the return force.

Figure 19:
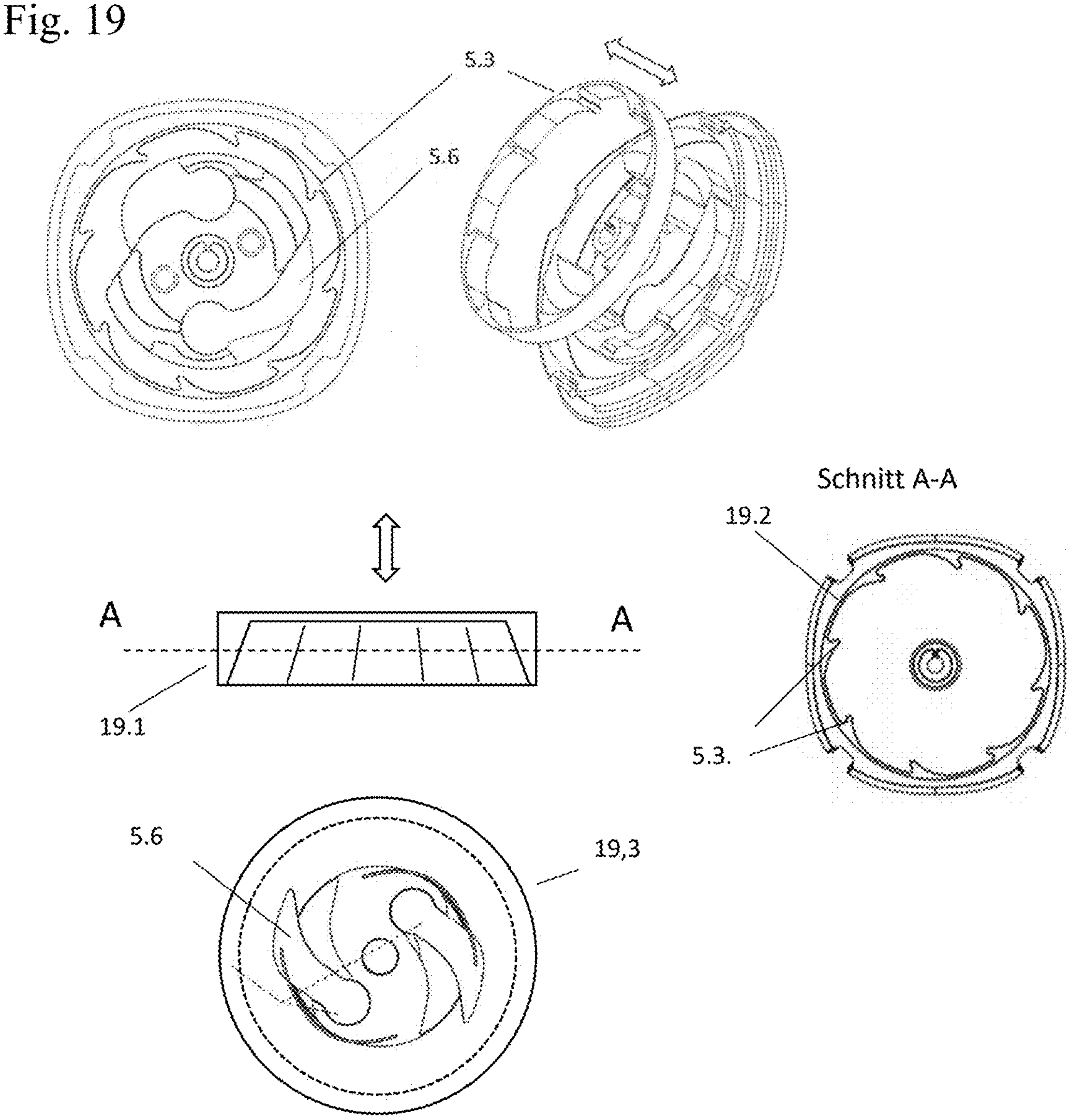
FIG. 19 is a schematic diagram showing a positive locking structure able to extend in an axial direction.

FIG. 19 shows the positive locking structure (5.3) able to extend in the axial direction and thus the blocking function able to be deactivated. Depicted is the retracted state which enables the blocking.

(19.1) shows a conical positive locking structure (5.3) in vertical section, (19.2) shows this structure through section AA (19.1) in plan view, and (19.3) shows the rotor with the contact elements (5.6) in plan view. When the positive locking structure (19.1) is axially displaced, the air gap changes and the contact elements (5.6) have to extend out to different distances, whereby the speed required thereto is different.

(5.3) can also be designed without a positive locking structure (also for (19.1)), whereby the rotation is decelerated as in the case of a drum brake.

The invention claimed is:

1. A blocking system for limiting physiological movements of body segments, wherein an extending element and a blocking element are configured to connect together the body segments such that the extending element is wound onto a winding mechanism in the blocking element, and a blocking mechanism configured to completely or partially block further rotation of the winding mechanism upon a specific speed being exceeded, wherein the blocking system comprises a resetting winding mechanism which allows a change in a length of the extending element in a specific range and is coupled to the blocking mechanism to transmit a force which blocks the winding mechanism by positive locking or friction, wherein the blocking mechanism prevents the change in the length and thus absorbs the force that occurs, and wherein the change in the length is realized by a coil or a reel onto which a flexible tension element in the form of a cord, a wire, a cable, a strap, a belt or a chain is rolled or looped around.

2. A blocking system according to claim 1, wherein the blocking system consists of at least one blocking unit configured to be worn on a body by way of at least two fixed connection points on variably connected ones of the body segments.

3. The blocking system according to claim 2, wherein the at least one blocking unit can either be triggered mechanically, electronically or by a combination thereof as well as in the blocking system in which the at least one blocking unit is connected wirelessly or via control lines to a central control and triggering device.

4. The blocking system according to claim 2, wherein the at least one blocking unit is coupled to oppositely disposed parts and to itself via a deflection mechanism.

5. The blocking system according to claim 1, wherein the blocking system is movable below a speed threshold.

6. The blocking system according to claim 1, wherein the blocking system initiates blockage below a speed threshold via the blocking mechanism.

7. The blocking system according to claim 1, wherein the blocking system is configured to fit with different body segments connected to each other individually or in combination via different joints, wherein, for example the joints are swivel joints, hinge joints, saddle joints, planar joint connections, condylar or ball joints.

8. The blocking system according to claim 1, wherein oppositely disposed parts of the blocking system can be connected to a body attachment structure by sewing, riveting, tying, gluing, welding, screwing, or wiring.

9. The blocking system according to claim 1, wherein the resetting winding mechanism is powered by an energy store situated in a linear voltage range.

10. The blocking system according to claim 1, wherein the flexible tension element is fixed thermally, mechanically or chemically in the resetting winding mechanism.

11. The blocking system according to claim 1, wherein a mechanical connection between the winding mechanism and the blocking mechanism is realized by V-belts, toothed belts, guide rollers, gears, friction or a shaft.

12. The blocking system according to claim 1, wherein the blocking system comprises a mechanical coupling in a form of a mounted receiving disk in which at least one contact element is rotatably mounted.

13. The blocking system according to claim 1, wherein the blocking mechanism can be activated by tension or pressure and is in mathematical relation to a cited threshold value.

14. The blocking system according to claim 1, wherein contact elements are mounted by means of pins or positive locking.

15. The blocking system according to claim 1, wherein contact elements form a bonding surface by way of a positive connection with a surrounding housing upon a threshold value being exceeded and thus effect blockage.

16. The blocking system according to claim 1, wherein the blocking mechanism triggers mechanically, electrically, electromagnetically, viscously, by centrifugal force or a combination thereof depending on a threshold value.

17. The blocking system according to claim 1, wherein one or more sensors are used to measure revolutions of a rotor of the blocking element which measure a position of a contact element either optically with reflected light sensors, magnetically with a detector coil, or a Hall sensor or with an ultrasonic sensor and are positioned in a stator housing on a circumference facing an interior or laterally in height facing the interior.

18. The blocking system according to claim 1, wherein a rotation is used to generate energy by a permanent magnet being positioned in a circumference of a rotating part on the or on one of end faces near the circumference, a moving magnetic field inducing a voltage in a coil in a stator.

* * * * *